United States Patent [19]

Francis

[11] Patent Number: 4,797,388

[45] Date of Patent: Jan. 10, 1989

[54] PHARMACEUTICAL COMPOSITIONS WITH GALACTITOL AS CARRIER

[75] Inventor: Daniel L. Francis, Ravenna, Ohio

[73] Assignee: Cetus Corporation, Emeryville, Calif.

[21] Appl. No.: 879,143

[22] Filed: Jun. 26, 1986

Related U.S. Application Data

[63] Continuation-in-part of Ser. No. 612,626, May 21, 1984, Pat. No. 4,659,699, which is a continuation-in-part of Ser. No. 524,899, Aug. 22, 1983, abandoned.

[51] Int. Cl.[4] .................... A61K 31/66; A61K 31/70; A61K 47/00
[52] U.S. Cl. ........................................ 514/23; 514/110
[58] Field of Search ................... 514/23, 54, 110; 536/17.1, 27, 29, 124, 55.3

[56] References Cited

U.S. PATENT DOCUMENTS

| | | | |
|---|---|---|---|
| 3,384,546 | 5/1968 | Palermo | 514/53 |
| 3,944,625 | 3/1976 | Neal | 556/146 |
| 3,993,781 | 11/1976 | Horvath et al. | 514/908 |
| 4,418,058 | 11/1983 | Hirai et al. | 514/232 |
| 4,446,134 | 5/1984 | Naito et al. | 424/101 |
| 4,537,883 | 8/1985 | Alexander et al. | 514/110 |
| 4,604,377 | 8/1986 | Fernandes et al. | 424/85 |
| 4,659,699 | 4/1987 | Francis | 514/53 |

FOREIGN PATENT DOCUMENTS

| | | |
|---|---|---|
| 0080879 | 6/1983 | European Pat. Off. . |
| 0133767 | 3/1985 | European Pat. Off. . |
| 0225581 | 6/1987 | European Pat. Off. . |
| 2078737 | 1/1982 | United Kingdom . |

OTHER PUBLICATIONS

Virkki; Chemical Abstracts vol. 88: 197643h (1978).
Aoki et al; Chemical Abstracts vol. 92: 220695v (1980).
Tashiro et al; Chemical Abstracts vol. 97: 138233n (1982).
Manankov; Chemical Abstracts vol. 98: 121377k (1983).
Minker et al; Chemical Abstracts vol. 103: 200871s (1985).
Marttila et al; Chemical Abstracts vol. 102: 12408b (1985).
Kovalcik et al., *Journal of Parenteral Science and Technology*, vol. 42, No. 1, pp. 29–38 (1988).

*Primary Examiner*—Ronald W. Griffin
*Assistant Examiner*—Nancy S. Carson
*Attorney, Agent, or Firm*—Albert P. Halluin

[57] ABSTRACT

An improved pharmaceutical composition contains galactitol as carrier for the therapeutic agent. One example is a lyophilized composition of about 20 parts by weight of cyclophosphamide, taken as the anhydride, about 5 to 21 parts by weight of galactitol as excipient, and about 1.4 to 3 parts by weight of water. Preferably, the amount of galactitol is 15–21 parts by weight. The galactitol enhances the chemical and physical stability of the drug and allows faster reconstitution of the formulation in water than mannitol.

16 Claims, No Drawings

PHARMACEUTICAL COMPOSITIONS WITH GALACTITOL AS CARRIER

This application is a continuation-in-part application of copending U.S. Ser. No. 612,626 filed May 21, 1984, now U.S. Pat. No. 4,659,699 issued Apr. 21, 1987 which is a continuation-in-part application of U.S. Ser. No. 524,899 filed Aug. 22, 1983, now abandoned.

BACKGROUND OF THE INVENTION

This invention relates to a pharmaceutical composition which is readily reconstitutable in water. In particular, this invention relates to a composition which contains galacticol as carrier for a therapeutic agent such as cyclophosphamide.

Cyclophosphamide is a widely used synthetic antineoplastic drug and immunosuppressive agent for the treatment of a variety of malignant and non-malignant diseases. It exists in two forms: anhydrous and monohydrate. The monohydrate form is employed in processing for clinical applications because the anhydrous form is not stable. At comparatively low relative humidity, the monohydrate will lose the water of hydration.

Cyclophosphamide has been made into unit dosage compositions by mixing the dry powder with sodium chloride to provide isotonicity when the product is reconstituted. The disadvantages of the dry powder blend include formation of mixtures of powders which are not pharmaceutically elegant, i.e., not of uniform appearance and/or consistency, contaminated with insoluble particulates, and having prolonged dissolution time when reconstituting into a solution.

The disadvantages of dry powder formulations have been addressed by lyophilizing an aqueous solution of the formulated material, to obtain a solid composition of improved stability. The advantages of lyophilization are (1) the solution of the drug can be filtered to remove particulates, and (2) the time required for reconstitution is significantly reduced. The lyophilized product also appears to be more stable to heat.

One patent which specifically addresses the lyophilization of cyclophosphamide is U.S. Pat. No. 4,537,883 issued Aug. 27, 1985. The formulation of this patent includes cyclophosphamide with mannitol as excipient and a range of moisture content of 1.25 to 2 parts by weight of water. The composition is shown to have improved physical stability over the dry formulation. It also shows enhanced appearance over the dry formulation and over lyophilizates incorporating lactose and other excipients.

It is an object of the present invention to identify another excipient which would yield a physically and chemically stable lyophilizate as an alternative to mannitol, and to identify a carrier for lyophilized pharmaceutical compositions which allows for faster reconstitution in water than mannitol. Surprisingly, of the other excipients besides mannitol, only galactitol exhibits the physical and chemical stability necessary for a feasible commercial product.

SUMMARY OF THE INVENTION

Accordingly, the present invention provides a pharmaceutical composition comprising a therapeutic agent and a carrier predominantly comprising a galactitol.

In a preferred embodiment, the invention herein provides a hydrated, rapidly reconstitutable lyophilizate composition, exhibiting enhanced chemical and physical stability as well as uniform consistency and appearance, which comprises about 20 parts by weight of cyclophosphamide, taken as the anhydride, about 5 to 21 parts by weight of galactitol, and about 1.4 to 3 parts by weight of water.

The composition may be reconstituted in vials with water or other suitable diluent to provide solution for oral or parenteral administration to patients.

While U.S. Pat. No. 4,537,883 discloses that only use of mannitol as the major excipient results in the desirable physical properties, applicant has discovered that galactitol may be used alone as excipient or, if desired, in combination with a minor amount (less than 50% by weight) of mannitol, to achieve outstanding physical, aesthetic, and chemical properties.

DESCRIPTION OF THE PREFERRED EMBODIMENTS

The invention which is contemplated herein encompasses using galactitol as the predominate carrier in pharmaceutical compositions. For example, a lyophilized composition of cyclophosphamide and galactitol exhibits both chemical and physical stability and an enhanced appearace. In addition, using galactitol results in faster reconstruction in water than using mannitol as carrier.

Galactitol is a polyol of the formula:

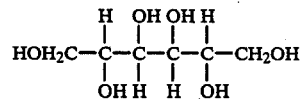

It is described in greater detail in the Merck Index, the disclosure of which is incorporated herein by reference.

The words "predominantly comprising galactitol" as used herein refer to the carrier being comprised of at least 50% by weight of galactitol.

The types of therapeutic agents which may be employed include any agent which exhibits a therapeutic (or curative) or prophylactic effect in a mammal, incuding human beings. Examples of such drugs include anti-cancer drugs, anti-autoimmunity (allergy) drugs, and anti-infective agents such as antibiotics, anti-viral agents, anti-fungal agents, anti-protozoal agents, anti-parasitic agents, and other agents which combat infections. Specific examples of these anti-infectives include monoclonal or polyclonal antibodies against Gram-negative sepsis and other infectious diseases, as well as more traditional drugs such as penicillin. A more complete list of therapeutic agents for purposes herein can be found in the *USAN and the USP Dictionary of Drug Names*, Griffiths et al., ed., U.S. Pharmacopeial Convention, Inc., Rockville, Md. 1985 and the *Physicians' Desk Reference*, 40th ed., Edward Barnhart, ed., Oradell, N.J.: Medical Economics Company Inc., 1986, the disclosures of both of which are incorporated herein by reference.

The preferred therapeutic agents herein are anti-cancer drugs, and more preferably are lymphokines and cytotoxic agents. The lymphokines may be any lymphokine such as, for example, interleukin-1 (IL-1), interleukin-2 (IL-2), interleukin-3 (IL-3), colony stimulating factor-1 (CSF-1), G-colony stimulating factor (G-CSF), GM-colony stimulating factor (GM-CSF), chemotoxins, migration inhibitory activity factor (MIF), macrophage-activating factor (MAF), NK cell activating factor, T cell replacing factor, leukocyte-inhibitory factor (LIF), osteoclast-activating factor (OAF), soluble immune response suppressor (SIRS), growth-stimulating factor, a monocyte growth factor, etc.

The cytotoxic agents may be any substance which is anti-tumor agent and include, for example, the preferred compounds interferon-$\alpha$ (IFN-$\alpha$), interferon-$\beta$ (IFN-$\beta$), interferon-$\gamma$ (IFN-$\gamma$), tumor necrosis factor (TNF), an immunotoxin such as an ovarian or breast cancer antibody conjugated to ricin A chain, cyclophosphamide, methotrexate, vincristine, 5-fluorouracil, cystosine arabinoside, vinblastine, bleomycin, doxorubicin hydrochloride, mitomycin-C, daunorubicin, and cisplatin. Most preferably, the therapeutic agent herein is cyclophosphamide, and the composition also contains water for formulation.

If the therapeutic agent is a protein, it may be from a native source or recombinantly produced. Also, it may be altered by replacing cysteine residues not essential for biological activity with another netural amino acid to improve the stability of the protein as described for IL-2 in U.S. Pat. No. 4,518,584 and for IFN in U.S. Pat. No. 4,588,585, the disclosures of which are incorporated herein by reference.

The dosage amount of therapeutic agent and the relative amount of galactitol to the therapeutic agent will depend mainly on the type of therapeutic agent and the use to which it will be put. For IL-2, for example, the unit dosage amount will range from about 0.01 to 2 mg, preferably 0.2 to 0.3 mg. The IL-2 will typically constitute about 0.015% to 3.85% by weight of the mixture of IL-2 and carrier, more preferably about 0.4% to 0.6%. Further details concerning IL-2 formulation may be found in U.S. Pat. No. 4,604,377, issued on Aug. 5, 1986, the disclosure of which is incorporated herein by reference.

The dosage amount of cisplatin is a maximum of 100 mg/m$^2$ twice per month. The dosage amount of vincristine is a maximum of 2 mg total dose three times a month. The dosage amount of 5-fluorouracil is a maximum of 1000 mg/m$^2$ for four days in a row once a month. The dosage amount of vinblastine is a maximum of 2 mg/m$^2$ per day for five days. The dosge amount of bleomycin is a maximum of 15 mg/m$^2$ daily for four days. The usual dosage amount of doxorubicin hydrochloride is 60 mg/m$^2$ once every 3-4 weeks. The maximum dosage amount of mitomycin-C is 20 mg/m$^2$ intraveneously as a single bolus once every three weeks. The maximum dosage amount of daunorubicin is 30-60 mg/m$^2$ every 3-4 weeks.

Further information of the amounts of each therapeutic agent to be placed in vials for formulation can be found in the *Physicians' Desk Reference*, 40th edition, supra, the disclosure of which is incorporated herein by reference. For example, Methotrexate for Injection is available in 20, 50, 100 and 250 mg single dose vials. Other drugs may be formulated in the same or different amounts depending on their physical, chemical and medical properties.

The relative amounts of galactitol to therapeutic agent in the formulation will range from about 1:0.1 to about 1.05:1 galactitol:agent, depending on the agent and its solubility characteristics. For example, when CPA is used as the therapeutic agent, the amount of galactitol is limited by solubility and cannot exceed as high as 1.05:1 galactitol:CPA as the anhydride.

The formulation herein may contain other other ingredients besides a carrier such as a detergent, e.g., sodium dodecyl sulfate, which may be required to solubilize lipophilic proteins such as recombinant IL-2 and IFN-$\beta$. In addition, the formulation may contain a small amount of buffer which will provide a physiological pH if the mixture is reconstituted.

The co-carrier which may be employed along with galactitol in an amount up to 49% by weight of total carrier must be water soluble, must not react with the therapeutic agent and must be stable. This carrier also is preferably non-sensitive (i.e., non-hygroscopic) to water. Examples of such co-carriers include lactose, mannitol, and albumin such as human serum albumin, but preferably mannitol. Most preferably, no co-carrier is employed.

The discussion and examples which follow relate to CPA specifically, which is the preferred embodiment, but is not the only embodiment of the invention herein.

The chemical stability of the composition for purposes herein is measured by its ability to retain its original potency after being exposed to a 37° C. temperature for one week. The physical stability of the composition for purposes herein is measured by its ability to retain its original physical properties (including color, dissolution rate, and consistency and uniformity of appearance) after exposure to a 37° C. temperature for one week, which is expected to correspond to being stable at 27°±3° C. for one year, and at 22°±3° C. for 3–5 years. Exposure of the composition to 37° C. is not uncommon for short periods during transportation or warehouse storage.

The enhanced appearance of the composition herein is measured by the uniformity of its consistency and appearance such as color, i.e., by the "pharmaceutical elegance" of the product. Pharmaceutical elegance refers to a visually pleasing product, a criterion commonly used by those skilled in the art to gauge the market quality of the pharmaceutical. In more quantitative terms, the pharmaceutically elegant product has a uniform appearance, i.e., when examined from outside a glass vial or other container in which the product is held, is essentially free from blisters, bubbles or voids which individually do not exceed 2 mm in equivalent diameter.

A uniform appearance and consistency also refers to a cake with uniform color, uniform moisture content, and not fissures or flaking as evidenced by plate-like flakes and granular odd-sized agglomerates.

While it is generally acknowledged that the visual appearance of cyclophosphamide product may not affect its pharmaceutical efficacy, purchasers and dispensers of pharmaceuticals expect lyophilized products to have pharmaceutical elegance which otherwise dry, powder-filled cyclophosphamide conspicuously lacks.

The preferred therapeutically active agent herein, CPA, is an anti-cancer agent with the chemical name: 2-[bis-(2-chloroethyl)amino]-tetrahydro-2H-1,3,2-oxazaphosphorine-2-oxide monohydrate. CPA is described in greater detail in U.S. Pat. No. 3,018,302 and the Merck Index, the disclosures of which are both incorporated by reference.

Lyophilization of an aqueous solution of CPA with the galactitol excipient under the conditions specified below results in a CPA product which has uniform CPA hydrate integrity and good shelf-life stability. "Hydrate integrity" means that the bound moisture content of the CPA hydrate is sufficient to provide stability of the product, which content is hypothesized to be in the range from 5% to 7% by weight of the CPA hydrate; and "uniform" means that substantially all vials in a batch of at least several hundred vials are lyophilized to within a moisture range of from about 1.4 to 3 parts by weight of water per about 20 parts by weight of CPA taken as the anhydride. The criticality of maintaining the CPA hydrate integrity is premised on the knowledge that the moisture content of the CPA product cannot be reduced below about 1.4 parts, because the CPA will degrade, and cannot exceed about 3 parts for the same reason. The particular proportioning of this moisture relative to each component of the product is not narrowly critical.

By a "dosage amount" of CPA is meant a specified amount of pure CPA (anhydrous), which may, if desired, include an overage, preferably up to 10%, and galactitol, optionally with a co-carrier such as, preferably, mannitol. The composition is in a single dose vial having a size sufficient to allow reconstitution with water or other suitable diluent such as, e.g., bacteriostatic Water for Injection to yield the appropriate concentration of CPA for administration. Typical dosage amounts herein are 100 mg, 200 mg, 500 mg, 1 g and 2 g of CPA, taken as the anhydride (not including an overage). An equivalent amount by weight of galactitol vis-a-vis CPA is preferred as excipient.

The amount of water effective for reconstitution and administration may range broadly, but is preferably 5 to 100 ml, more preferably 15–75 ml.

A typical dosage amount is 500 mg CPA, taken as the anhydride, and 525 mg galactitol reconstituted in 20 ml water, or 500 mg CPA, taken as the anhydride, and 525 mg galactitol reconstituted in 25 ml water.

The galactitol in the formulation herein may be replaced, in part, by a minor amount of mannitol as excipient, with no adverse effects. By minor amount is meant that no more than 49% by weight of the galactitol can be so replaced.

The amount of galactitol present in the formulation may range from about 5 to 21 parts by weight of the final formulation, given about 20 parts by weight of CPA, taken as the anhydride. If the amount of galactitol exceeds about 21 parts the product is no longer soluble. If the galactitol amount is too low, however, the product will be harder to lyophilize. Preferably the amount of galactitol employed is 15 to 21 parts by weight, more preferably 20–21 parts by weight.

The cake of the CPA product has a uniform, near-white color and is essentially free of flaking or granula agglomerates.

As mentioned above, the CPA product herein contains about 1.4 to 3 parts by weight of water per 20 parts by weight of CPA, taken as the anhydride. Such a product provides the requisite shelf-life stability which is evidence that the integrity of the CPA hydrate is maintained. Moisture determination is made by any standard method, as, for example, described in Edwards, *Freeze-Drying Handbook*, by Terence W. G. Rowe and John W. Snowman, published by Edwards High Vacuum: Crawley, England (1976).

The size of the vial chosen is determined by the dosage amount, the basic dosage amount of CPA (e.g., 500 mg of CPA) being provided in vials which can hold 20 ml to 50 ml, and most preferably 25 or 30 ml. Most preferred for a basic dosage amount is a 30 ml vial in which 15 ml of solution is added containing 500 mg of CPA (anhydride), about 525 mg of galactitol, and a quantity of water or other suitable diluent sufficient (QS) to bring the volume to 15 ml.

Precisely how the lyophilization cycle is monitored is not critical and this may be effected in various ways, for example, as suggested in *Freeze Drying Processes for the Food Industry*, by Gutcho, M. H., published by Noyes Data Corporation, New Jersey (1977). The essential elements of the cycle are the monitoring of the temperature of the shelves, the temperature of the material in the vials, and the time periods during which the temperature and pressure conditions are controlled.

The chamber is evacuated after the vials are frozen and a temperature from about −20° C. to about −50° C. is maintained for enough time to ensure that all the vials are at substantially the same temperature. The temperature may be determined by probes in vials racked in a tray placed on a shelf of the lyophilization chamber. A higher temperature may be used if time is not a factor, but temperatures much warmer than −20° C. are not economical. A pressure of no more than 1000 micrometers is essential, and it is preferred to use a pressure in the range from about 10 to 500 micrometers, which may be effected with any conventional high-quality vacuum pump. The time during which the chamber is evacuated is not critical as long as the material in the vials is frozen solid, a typical evacuation period ranging from about 10 minutes to about one hour.

The shelf temperature is raised gradually, the rate being controlled by a control means such as a cam, or microprocessor, or by manual control, so that the shelf temperature reaches a finish-drying temperature no higher than that which deleteriously affects the CPA material. Too high a temperature causes the material to melt or otherwise be degraded, adversely affecting both its pharmaceutical efficacy and elegance.

The vacuum is maintained throughout the drying cycle, and in all cases should be sufficient to produce dried material with a moisture content of less than 2% by weight based on total net content weight of the dried material (corresponding to less than 1.3 parts by weight water per 20 parts by weight of CPA). The period of time will depend upon the dosage amounts in the vials, the size and configuration of the vials, and the number of vials in an assembly in the particular chamber being used.

After the vials have been dried to the aforespecified degree in the first stage of the process, the lyophilized material is rehydrated by introducing water vapor into the chamber. A fine spray of water may be jetted intermittently into the chamber in an amount sufficient to raise the moisture level in the chamber to at least 75% relative humidity. Any source of pure water may be used, but clean steam is preferred because it is convenient and lends itself to precise control. Sufficient clean steam is introduced over a period of time sufficient (generally in the range from about five minutes to about two hours) to attain a relative humidity of at least 75%, preferably about 75–80%, in the chamber. The humidity is maintained at this level until it is determined that the material in the vials has absorbed enough moisture to meet the water content range specified above.

The exact relative humidity of the chamber for rehydration is not critical if it is at least 75%, it being evident that rehydration will take place when the vapor pressure in the chamber is greater than that of the lyophilized material. The relative humidity is preferably 75–80% because at lower humidity the rehydration is impractical.

Rehydration of the lyophilized material obtained after the first stage may be effected not only by using steam, but also by the following methods:

A. The vials of lyophilized material are removed from the lyophilization chamber and placed in a constant humidity cabinet at 75-80% relative humidity for rehydrating the material. The material is held in the constant humidity cabinet until it is determined that the material in the vials has absorbed enough moisture to meet the critical moisture content of CPA product. The vials of rehydrated CPA product are then removed from the constant humidity cabinet and stoppered.

B. The vials of lyophilized material are placed in a chamber over a constant humidity solution with a relative humidity value of 80-90%. The material is held in the chamber over the solution until it is determined that the material has absorbed enough moisture to meet the specification of the critical moisture content of CPA product. At the end of the rehydration step, the probes in the vials read about $+20°$ C., without exceeding about $+25°$ C. for any significant period of time.

In an analogous manner, the process may be carried out in vials in which a dosage amount includes less than an equivalent weight of the excipient.

The following examples are provided to illustrate further the embodiments of the invention. In the examples, all parts and percentages are by weights and all temperatures are in degrees Centigrade unless otherwise noted.

EXAMPLE I

A preparation of a 500 mg/vial dosage amount of CPA hydrate with 525 mg/vial galactitol for 15 cc/vial Water For Injection (WFI) was prepared as follows:

A total of 29.60 g of cyclophosphamide monohydrate and 28.88 g of galactitol were added to 700 ml of WFI and mixed vigorously for one hour using a high-speed mixer. The resulting solution was clear and colorless.

The solution was brought to volume of 825 ml with WFI, and the solution was mixed for five minutes. The result was a clear, colorless solution at pH 3.95.

The solution was filtered through a 47 mm Pall NR 0.2μ membrane using a 47 mm Millipore TM Millitube TM filter holder. The solution, which filtered easily at 40 psi, was very clear and colorless.

The solution was dispensed in 53×30-cc Flint, Type I, molded vials (Wheaton) at 15 ml/vial, with closures placed in lyophilizing position, racked in trays and placed on the shelves of a lyophilization chamber.

In the first stage of lyophilization, the product solution in the vials was frozen to a temperature of about $-20°$ C., and after all the probes reached the desired temperature, this temperature was maintained for about two hours. The condenser was chilled to about $-50°$ C. and the chamber was evacuated, the vacuum being adjusted with a $N_2$-sweep to read in the range from about 10 to about 1000 micrometers. The shelves were then warmed to about $+22°$ C., and when the probes in the vials read about $+20°$ C., lyophilization cycle was continued for about 4 to 24 hours without exceeding about $25°\pm2°$ C. for any significant period of time.

In the second stage, rehydration of the lyophilization material was accomplished by introducing water vapor directly into the chamber until it reached about 75-80% relative humidity at 25° to 30° C., the water being in the form of clean steam passed through a sterile microbiological filter. When the chamber had reached an equilibrium value of about 80% to about 85% relative humidity, this humidity was maintained until the product acquired a moisture content of about 3.60% by weight based on the total weight of the formulated product, with 3.3% being equivalent to 1.3 parts per 20 parts CPA.

The moisture level was monitored periodically by removing representative samples (vials) in the lot and carrying out the standard Karl Fischer analysis.

Before rehydration all vials possessed solid, uniform snow-white cakes. The initial moisture content was 0.19% by weight, based on CPA as the anhydride.

After rehydration the moisture content and appearance were as follows:

| Hours of Rehydration | % Water (by weight, based on net CPA product) | Appearance |
| --- | --- | --- |
| 1 | 0.90 | Uniform snow-white cakes |
| 2 | 1.36 | Uniform snow-white cakes |
| 4 | 2.10 | Uniform snow-white cakes |
| 6 | 2.64 | Uniform snow-white cakes |
| 8 | 3.10 | Uniform snow-white cakes |
| 10 | 3.60 | Uniform snow-white cakes |

The minimum moisture requirement is 3.30% (1.3 parts by weight per 20 parts by weight CPA).

The remaining samples were placed on a stability testing program in controlled atmosphere rooms at a temperature of $24°\pm2°$ C., and at 75% relative humidity at temperatures of 37° C. and $30°\pm2°$ C.

Samples of vials (3 for each test interval) were taken at random from each batch and analyzed at the intervals indicated, and the results recorded in the following Table I. The assays were performed according to the procedure described in the USP monograph for Cyclophosphamide for Injection. The variation in assay results is within the specified range of 90-110% CPA set forth in the USP monograph. Degradation, indicating a lack of adequate chemical stability, would be evidenced at the end of a test period by a significantly lower assay than the initial assay. As will be evident from the representative tests set forth below, there was no evidence of degradation at the end of two months at $30°\pm2°$ C. The reconstitution time was ten seconds as opposed to at least one minute for formulations containing only mannitol as carrier.

TABLE I

| Dosage Amount | HPLC Analysis (% potency) | pH | % Moisture K. Fischer | Reconstit'n Time (Sec.) |
| --- | --- | --- | --- | --- |
| | Initial | | | |
| 500 mg | 98 | 4.00 | 3.60 | 10 |
| | After One Month | | | |
| | (37° C.) 91% | 4.00 | 3.60 | 10 |
| | (30 ± 2° C.) 98% | 4.00 | 3.60 | 10 |
| | After Two Months | | | |
| | (37° C.) 49% | 2.95 | N/A | 10 |
| | (30 ± 2° C.) 98% | 3.95 | N/A | 10 |

This data show stability expected to correspond to room temperature stability for 3-5 years.

EXAMPLE II

Use of Excipients Other Than Galactitol

1. A total of 535 mg per vial of CPA, taken as the anhydride, was mixed with 950 mg per vial of one of the following excipients (A) xylitol, (B) inositol, (C) mannose, (D) maltose, or (E) fructose to 85% (about 320-340 ml) of total QS volume (15 cc). Lots A–D were stirred vigorously for one hour using a high-speed mixer, and Lot E was stirred for 15 minutes. The solutions were filled to 375 ml with WFI, mixed for 10 minutes, and filtered through a membrane at 40 psi (0.12 mPa).

Twenty-two vials per lot at 15 cc per vial were placed into an Edwards lyophilization chamber and lyophilized as described in Example I. The results are provided in Table II.

TABLE II

| Lot No. | Appearance |
|---|---|
| A | Totally melted and glazed, cake shrunken to the vial bottom; all vials rejected |
| B | Totally melted and glazed, cake shrunken to the vial bottom; all vials rejected |
| C | Shrunken and molten glass appearance; all vials rejected |
| D | All vials possessed solid uniform snow-white cakes; no rejects occurred |
| E | Clear, melted, wet and sticky cakes; poor appearance |

When Lot D was tested for stability it was found to lose its potency and solubility characteristics after exposure to 37° C. for one week.

2. A total of 500 mg per vial of CPA, taken as the anhydride, was mixed with one of the following excipients: (A) 500 mg/vial of dextran and 125 mg per vial of sucrose, (B) 500 mg/vial of maltodextrin (Grain Processing Corp., Miscatine, Iowa.), (C) 1000 mg/vial of dextran, or (D) mg/vial of maltodextrin.

A total of 9.70 g of CPA was mixed with the appropriate amount of excipient in 230 ml of WFI and mixed vigorously with a high-speed mixer. The solutions were brought to the volume of 270 ml with WFI and mixed for 2–3 minutes. This mixture was filtered through a membrane and dispensed in 17 vials per lot. The vials were placed in a lyophilization chamber and lyophilized as described in Example I. The results before and after rehydration are shown in Table III, where HPLC analysis was made after storage for 6.5 days at 37° C. and 75% relative humidity, and % moisture is expressed by weight based on CPA as the anhydride.

TABLE III

| | Before Rehydration | | After Rehydration for 35 min. at 83% relative humidity using live steam | | |
|---|---|---|---|---|---|
| Lot No. | % Moisture | Appearance | % Moisture | Appearance | HPLC Analysis (% potency) |
| A | 0.25 | Solid, uniform white cakes; no shrinkage | 9.02 | Solid, uniform white cakes | 97.3 |
| B | 3.45 | Solid, uniform white cakes; no shrinkage | 8.62 | Solid, uniform white cakes | 98.1 |
| C | 0.06 | Solid, uniform white cakes; no shrinkage | 7.46 | Solid, uniform white cakes | 96.8 |
| D | 0.18 | White cakes; slight shrinkage | 9.07 | White cakes; slight shrinkage | 97.5 |

The mixtures were processed as described above, and the results of appearance and stability after rehydration are indicated in Table IV, with HPLC analysis made after storage for 6.5 days at 37° C. and 75% relative humidity.

TABLE IV

Seven Day Stability Results
(Storage at 37° C./75% Relative Humidity)

| Lot No. | Appearance | HPLC Analysis (% potency) |
|---|---|---|
| A | Shrunken, almost melted, orange-brown cakes; poor appearance | 75 |
| B | Snow-white, slightly shrunken cakes | 88.6 |
| C | Snow-white, uniform cakes; good appearance | 75.1 |
| D | Snow-white, shrunken cakes | 96.8 |

3. A total of 500 mg per vial of CPA, taken as the anhydride, was mixed with one of the following excipients: (A) 250 mg per vial maltodextrin, or (B) 500 mg per vial maltodextrin.

The mixtures were processed as described above and mixed for five minutes, and the results of appearance before and after rehydration and stability after rehydration are indicated in Table V, with HPLC analysis made initially and after two-weeks' storage at 37° C. and 75% relative humidity.

TABLE V

| | | HPLC Analysis (% potency) | |
|---|---|---|---|
| Lot No. | Appearance | 0 | 2 weeks |
| A | Solid, uniform white cake before rehydration | 97.0 | 92.4 |
| B | Solid, uniform white cake before rehydration; shrunken off-white cake after two-weeks' storage at 37° C. | 98.4 | N/D* |

*N/D = Not determined

The results indicate that of all the above-tested excipients, which include monosaccharides, disaccharides, and polysaccharides, only galactitol successfully yielded a product on a caliber with mannitol with adequate chemical and physical stability as defined herein and uniform appearance and consistency. Yet, formulations using an excipients dextran and sucrose, maltodextrin, and dextran met the definition of "stability" in U.S. Pat. No. 4,537,883 and would have been declared as acceptable excipients under the criteria in that patent. Furthermore, the lyophilizate formulated with galactitol instantly reconstituted in water, whereas the lyophilizate formulated with mannitol alone required about one minute for reconstitution in water.

Other modifications of the above-described embodiments of the invention which are obvious to those of ordinary skill in the area of pharmaceutical formulation and related disciplines are intended to be within the scope of the following claims.

What is claimed is:

1. A hydrated lyophilizate composition, having enhanced chemical and physical stability and uniform appearance and consistency, comprising about 20 parts by weight of cyclophosphamide, taken as the anhydride, about 5 to 21 parts by weight of galactitol, and about 1.4 to 3 parts by weight of water.

2. The composition of claim 1 wherein the amount of galactitol is about 15 to 21 parts by weight.

3. The composition of claim 2 wherein the amount of galactitol is about 20 to 21 parts by weight.

4. The composition of claim 1 wherein no more than 49% by weight of the galactitol is replaced with mannitol.

5. A formulation comprising the composition of claim 3 comprising a dosage amount of cyclophosphamide in a vial sufficiently large to accommodate an effective amount of water to reconstitute the composition for administration.

6. The formulation of claim 5 wherein the dosage amount is selected from the group consisting of 100 mg, 200 mg, 500 mg, 1 g, and 2 g of cyclophosphamide, taken as the anhydride.

7. The formulation of claim 6 wherein the amount of water for reconstitution ranges from 5 to 100 ml.

8. The formulation of claim 7 wherein the amount of water for reconstitution ranges from 15 to 75 ml.

9. The formulation of claim 6 wherein the dosage amount is 100 mg of cyclophosphamide, taken as the anhydride.

10. The formulation of claim 6 wherein the dosage amount is 200 mg of cyclophosphamide, taken as the anhydride.

11. The formulation of claim 6 wherein the dosage amount is 500 mg of cyclophosphamide, taken as the anhydride.

12. The formulation of claim 11 wherein the amount of water for reconstitution ranges from 20 to 25 ml.

13. The formulation of claim 12 wherein the amount of galactitol is 525 mg and the amount of water is 20 ml.

14. The formulation of claim 12 wherein the amount of galactitol is 525 mg and the amount of water is 25 ml.

15. The formulation of claim 6 wherein the dosage amount is 1 g of cyclophosphamide, taken as the anhydride.

16. The formulation of claim 6 wherein the dosage amount is 2 g of cyclophosphamide, taken as the anhydride.